United States Patent [19]

Hagen et al.

[11] 4,263,430

[45] Apr. 21, 1981

[54] 2-METHYL-5-(2-HYDROXYSTYRYL)-1,3,4-THIADIAZOLE

[75] Inventors: Helmut Hagen, Frankenthal; Peter C. Thieme; Albrecht Franke, both of Wachenheim, all of Fed. Rep. of Germany

[73] Assignee: BASF Aktiengesellschaft, Fed. Rep. of Germany

[21] Appl. No.: 30,886

[22] Filed: Apr. 17, 1979

[30] Foreign Application Priority Data

Apr. 28, 1978 [DE] Fed. Rep. of Germany ....... 2818766

[51] Int. Cl.³ .................. C07D 285/12; A61K 31/424
[52] U.S. Cl. ..................................... 542/458; 424/270
[58] Field of Search ........................................ 542/458

[56] References Cited

FOREIGN PATENT DOCUMENTS 2624918 12/1977 Fed. Rep. of Germany .

Primary Examiner—Donald G. Daus
Assistant Examiner—D. B. Springer

Attorney, Agent, or Firm—Keil & Witherspoon

[57] ABSTRACT

2-Methyl-5-(2-hydroxystyryl)-1,3,4-thiadiazole of the formula

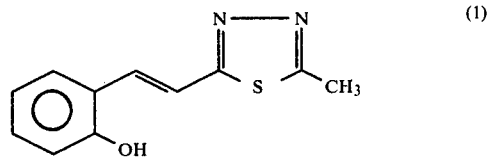

(1)

and processes for its preparation by condensing salicylaldehyde with 2,5-dimethyl-1,3,4-thiadiazole or 2-methyl-5-(triphenylphosphine-methylene)-1,3,4-thiadiazole. 2-Methyl-5-(2-hydroxystyryl)-1,3,4-thiadiazole is a valuable intermediate for the preparation of pharmacologically active compounds; for example the alkylamino-hydroxypropyl ethers can, because of their β-sympatholytic action, be used as drugs for the treatment of coronary diseases of the heart, cardiac arrhythmias and hypertonia.

1 Claim, No Drawings

2-METHYL-5-(2-HYDROXYSTYRYL)-1,3,4-THIADIAZOLE

The present invention relates to 2-methyl-5-(2-hydroxystyryl)-1,3,4-thiadiazole of the formula 1

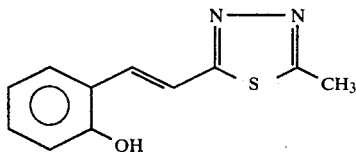

and to processes for its preparation. 2-Methyl-5-(2-hydroxystyryl)-1,3,4-thiadiazole is a valuable intermediate for the preparation of pharmacologically active compounds.

2-Methyl-5-(2-hydroxystyryl)-1,3,4-thiadiazole is prepared by condensing salicylaldehyde with 2,5-dimethyl-1,3,4-thiadiazole.

The condensation may be effected by reacting the two starting compounds directly or in an inert solvent.

Suitable solvents are relatively high-boiling solvents which under atmospheric pressure permit a reaction temperature of from 120° to 200° C. Examples of suitable solvents are relatively high-boiling aromatic hydrocarbons, eg. xylenes, and decalin, high-boiling alcohols and polyols and their ethers, eg. ethylene glycol and ethylene glycol methyl ether, and mixtures of the above. If the reaction is carried out in a hydrocarbon, the water formed during the reaction is advantageously removed by using a water separator.

The dimethylthiadiazole and salicylaldehyde are advantageously employed for the reaction in a molar ratio of from 5:1 to 2:1.

The condensation reaction temperature is from 120° to 200° C., advantageously from 140° to 170° C.

The condensation reaction can advantageously be catalyzed by means of weak Lewis acids, for example chlorides of zinc, tin, copper, mercury and iron. $ZnCl_2$ is particularly suitable, an advantageous amount to use being from 0.1 to 1 mole %. However, the reaction can also be carried out with comparable yields without using a catalyst.

The reaction is in general complete in from 10 to 40 hours, preferably from 15 to 20 hours. It may be advantageous to pass an inert gas, for example nitrogen, through the mixture whilst carrying out the condensation reaction.

Compound (1) according to the invention is preferentially produced in the trans-form. Material in the cis-form, produced at the same time, can readily be separated off by conventional physico-chemical methods, for example by recrystallization.

In another process for the preparation of 2-methyl-5-(2-hydroxystyryl)-1,3,4-thiadiazole, 2-methyl-5-(triphenylphosphine-methylene)-1,3,4-thiadiazole of the formula

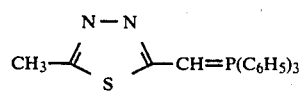

is reacted with salicylaldehyde.

This reaction is carried out in the conventional manner, for example as described in Houben-Weyl, volume 5/lb, pages 383 et seq.

The base, to effect conversion to the ylide, and the salicylaldehyde, are added successively to the alcoholic solution or suspension of the phosphonium salt, prepared from 2-chloromethyl-5-methyl-1,3,4-thiadiazole and triphenylphosphine in acetonitrile at the boil.

Suitable alcohols are, in particular, methanol and ethanol, and a particularly advantageous base to use is the alcoholate of the alcohol concerned, eg. sodium methylate or sodium ethylate. Since the ylides are as a rule sensitive to oxygen and water, it is advantageous to carry out the reaction in an anhydrous solvent and, where appropriate, under an inert gas. The reaction is carried out at room temperature, viz. at about 20° C.

2-Methyl-5-(2-hydroxystyryl)-1,3,4-thiadiazole, according to the invention, is a valuable intermediate for the synthesis of pharmacologically active compounds. For example, alkylation with an epihalohydrin or an α,ω-dihalo-2-propanol, followed by reaction with an amine, gives an amino-derivative of the general formula (2)

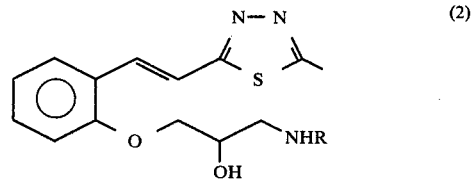

where R is in particular alkyl of 3 to 6 carbon atoms branched at the carbon in the α-position to the nitrogen, and unsubstituted or substituted by alkoxy of 1 to 3 carbon atoms, or is alkenyl or alkynyl of 2 to 8 carbon atoms or cyclopropyl, or an acid addition salt thereof. These compounds, because of their β-sympatholytic action, may be used for the treatment of coronary diseases of the heart, cardiac arrhythmias and hypertonia.

The Examples which follow illustrate the process for the preparation of 2-methyl-5-(2-hydroxystyryl)-1,3,4-thiadiazole. 2,5-Dimethyl-1,3,4-thiadiazole is prepared by methods disclosed in the literature, for example as described in German Laid-Open Application DOS No. 2,132,019.

EXAMPLE 1

570 g of 2,5-dimethyl-1,3,4-thiadiazole and 275 g of salicylaldehyde are mixed and slowly heated to 150° C. whilst passing nitrogen through the mixture. The mixture is then kept at 150° C. for 30 hours, after which it is cooled, excess 2,5-dimethyl-1,3,4-thiadiazole is distilled off and the residue is recrystallized from methylglycol. 304 g (56% of theory) of yellow crystals of melting point 253°–254° C. are obtained.
$C_{11}H_{10}N_2OS$ (218)
calculated: C 60.6 H 4.6 N 12.8. found: C 59.8 H 4.6 N 12.4.

EXAMPLE 2

0.5 g of $ZnCl_2$ is added to 57 g of 2,5-dimethyl-1,3,4-thiadiazole and 27.5 g of salicylaldehyde and the mixture is kept for 16 hours at 150° C., whilst stirring. When the mixture has cooled, unconverted 2,5-dimethyl-1,3,4-thiadiazole is distilled off. The residue is recrystallized from butyl acetate. 35.6 g (65% yield) of yellow crystals of melting point 252.5°–254.5° C. are obtained.

EXAMPLE 3

57 g of 2,5-dimethyl-1,3,4-thiadiazole and 27.5 g of salicylaldehyde are dissolved in xylene and the solution is refluxed for 48 hours. During the reaction, the water formed is removed by means of a water separator. When the mixture has cooled, the xylene and excess starting material are distilled off. The residue is recrystallized from methylglycol in the presence of animal charcoal. 22.3 g (41% yield) of yellow crystals of melting point 253°–254° C. are obtained.

EXAMPLE 4

(a) 2-Methyl-5-triphenylphosphoniummethyl-1,3,4-thiadiazole chloride 148 parts of 2-chloromethyl-5-methyl-1,3,4-thiadiazole and 261 parts of triphenylphosphine in 600 parts by volume of acetonitrile are refluxed for 4 hours. When the mixture has cooled to 20° C., the salt which has precipitated is filtered off. 348 g (85% of theory) of 2-methyl-5-triphenylphosphoniummethyl-1,3,4-thiadiazole chloride of melting point 288° C. (after recrystallization from ethanol) are obtained.

(b) 2-Methyl-5-(2-hydroxystyryl)-1,3,4-thiadiazole.

50 parts of a 30 percent strength by weight solution of sodium methylate in methanol are added to a suspension of 102 parts of 2-methyl-5-triphenylphosphoniummethyl-1,3,4-thiadiazole chloride in 200 parts by volume of ethanol at 20° C. 31 parts of salicylaldehyde are then added dropwise to the ylide which has precipitated. After stirring the mixture for one hour at 20° C., the solid which has precipitated is filtered off, washed with water and dried. 35 parts (65% of theory) of 2-methyl-5-(2-hydroxystyryl)-1,3,4-thiadiazole of melting point 269° C. (after recrystallization from dimethylformamide) are obtained. The higher melting point shows that the compound is virtually entirely in the trans-form, as can be demonstrated by NMR spectroscopy.

Examples of compounds of the formula (2), which may be used as addition salts with a physiologically acceptable acid are 2-methyl-5-[2-(2-hydroxy-3-isopropylamino-propoxy)-styryl]-1,3,4-thiadiazole, 2-methyl-5-[2-(2-hydroxy-3-cyclopropylamno-propoxy)-styryl]-1,3,4-thiadiazole, 2-methyl-5-[2-(2-hydroxy-3-tert.-butylamino-propoxy)-styryl]-1,3,4-thiadiazole and 2-methyl-5-[2-(2-hydroxy-3-(1-butyn-3-ylamino)-propoxy)-styryl]-1,3,4-thiadiazole.

The beta-sympatholytic action of the compounds was tested on cats. The conventional beta-sympatholytic agent propranolol was used as a comparative substance. The following test methods were used:

1. Beta-sympatholytic action

Isoproterenol (1 μg/kg, administered intravenously) increases the pulse rate of narcotized cats (weighing 2–4 kg) by an average of 40%. Beta-sympatholytic agents inhibit the tachycardia. Isoproterenol was administered before, and 10 and 40 minutes after, the intravenous administration of the test substances. There is a linear relation between the logarithm of the dose (mg/kg) of test substance administered and the inhibition (%) of isoproterenol tachycardia. From these relationships, the ED50%, ie. the doses which inhibit the isoproterenol-induced tachycardia by 50%, were determined.

2. Acute toxicity

To determine the mean lethal dose (LD50), the substances were administered intraperitoneally to female NMRI mice (weighing from 19 to 26 g).

The results summarized in the Table show that the substances exhibit an unusually high beta-sympatholytic activity. The cardiac beta-1-receptors, which are important in respect of pharmacotherapeutic use, are blocked by doses which are smaller by a factor of from 12 (compound 4) to 25 (compound 5) than the required doses of the comparative substance propranolol. It follows from this high activity, and from the lethal doses, which are of the same order of magnitude as for propranolol, that the therapeutic range is increased to from 7.6 times (compound 4) to 30.7 times (compound 6) that of propranolol.

TABLE

| | Beta-sympatholytic action and acute toxicity | | | | |
|---|---|---|---|---|---|
| | Beta-sympatholytic action[1] | | Acute toxicity | Therapeutic range 5 | |
| Substance | ED50%[2] | R.A.[3] | LD50[4] | absolute | relative[6] |
| Propranolol | 0.141 | 1.00 | 108 | 766 | 1.00 |
| Compound 3 | 0.010 | 14.10 | 83.0 | 8,300 | 10.84 |
| Compound 4 | 0.012 | 11.75 | 69.4 | 5,780 | 7.55 |
| Compound 5 | 0.000559 | 25.22 | 58.8 | 10,520 | 13.73 |
| Compound 6 | 0.0111 | 12.70 | 261 | 23,500 | 30.68 |

[1]Inhibition of isoproterenol-induced tachycardia in cats under hexobarbital narcosis. Compound administered intravenously.
[2]Dose (mg/kg) which inhibits the isoproterenol-induced tachycardia by 50%.
[3]Relative activity. Propranolol = 1.00.
[4]Mice, intravenous administration.
[5] $\frac{LD\ 50}{ED\ 50\%}$
[6]Propranolol = 1.00

Agents or formulations which in addition to conventional excipients and diluents contain a compound of the formula (2) as the active ingredient are prepared by conventional methods. Suitable individual doses for man are from 1 to 100 mg, preferably from 2 to 50 mg.

Compound 1

2-Methyl-5-[2-(2,3-epoxypropoxy)-styryl]-1,3,4-thiadiazole 3.72 g (0.085 mole) of 55% strength sodium hydride in paraffin oil are suspended in 150 ml of absolute tetrahydrofuran and 18.6 g (0.085 mole) of 2-(2-hydroxystyryl)-5-methyl-1,3,4-thiadiazole in 200 ml of absolute hexamethylphosphotriamide are then added dropwise in the course of 1.5 hours at from 0° to 3° C. Stirring is continued at room temperature for 1 hour, after which 11.7 g (0.085 mole) of dibromohydrin are added dropwise. The solution is left to stand at room temperature for 16 hours, after which it is poured onto 1.5 liters of ice water and 0.5 liter of saturated sodium chloride solution. The precipitated solid is filtered off and recrystallized from acetone. 11.8 g (51% of theory) of yellow crystals, of melting point 134°–135° C. are obtained.

$C_{14}H_{14}N_2O_2S$ (274)

calculated: C 61.3 H 5.1 O 11.7 S 11.7 N 10.2. found: C 61.3 H 5.4 O 13.5 S 10.5 N 8.4.

Compound 2

2-Methyl-5-[2-(2-hydroxy-3-chloro-propoxy)-styryl]-1,3,4-thiadiazole 1 g of 2-methyl-5-[2-(2,3-epoxypropoxy)-styryl]1,3,4-thiadiazole is left to stand in a mixture of 100 ml of ethanol and 5 ml of a 3 N solution of hydrogen chloride in ether for 12 hours. The precipitate formed is filtered off, washed neutral with ether and chromatographed on silica gel, using chloroform. Evaporation to dryness of the eluates containing the product gives spectroscopically pure 2-methyl-5-[2-(2-hydroxy-3-chloro-propoxy)-styryl]-1,3,4-thiadiazole of melting point 168°–170° C.

1H-NMR spectrum (CDCl$_3$, with TMS as the internal standard) $\tau = 2.5-3.3$ (m, 6H), 4.8 (s, 1H), 5.5–6.0 (m, 3H and OH), 6.1–6.3 (m, 2H) and 7.3 (s, 3H)

Compound 3

2-Methyl-5-[2-(2-hydroxy-3-isopropylamino-propoxy)-styryl]-1,3,4-thiadiazole 7 g (0.025 mole) of 2-methyl-5-[2-(2,3-epoxypropoxy)-styryl]-1,3,4-thiadiazole and 2.9 g (0.05 mole) of isopropylamine are mixed in 100 ml of isopropanol and the mixture is refluxed for 7 hours. On cooling, a precipitate forms; this is recrystallized from toluene, together with the solid residue obtained from concentrating the mother liquor. 5.1 g (61% of theory), melting point 156°–157°.

$C_{17}H_{23}O_2N_3S$ (333)

calculated: C 61.2 H 7.0 N 12.6. found: C 60.8 H 6.8 N 12.1.

Compound 4

2-Methyl-5-[2-(2-hydroxy-3-cyclopropylamino-propoxy)-styryl]-1,3,4-thiadiazole 3.8 g (0.014 mole) of 2-methyl-5-[2-(2,3-epoxypropoxy)-styryl]-1,3,4-thiadiazole and 1.0 g (0.018 mole) of cyclopropylamine are reacted similarly to the Example relating to compound 3. 2.2 g (48% of theory) of yellow crystals, of melting point 144°–145° C., are obtained from toluene.

$C_{17}H_{21}N_3O_2S$ (331)

calculated: C 61.6 H 6.4 N 12.7. found: C 60.8 H 6.1 N 12.3.

Compound 5

2-Methyl-5-[2-(2-hydroxy-3-tert.-butylamino-propoxy)-styryl]-1,3,4-thiadiazole 7 g (0.025 mole) of 2-methyl-5-[2-(2,3-epoxy-propoxy)styryl]-1,3,4-thiadiazole and 2.1 g (0.028 mole) of tert.butylamine are reacted similarly to the Example relating to compound 3. 3.8 g (44% of theory) of yellow crystals, of melting point 110°–112° C., are obtained from toluene.

$C_{18}H_{25}N_3O_2S$ calculated: C 62.2 H 7.2 N 12.1. found: C 62.3 H 7.3 N 11.6.

Compound 6

2-Methyl-5-[2-(2-hydroxy-3-(1-butyn-3-ylamino)-propoxy)styryl]-1,3,4-thiadiazole 6 g (0.022 mole) of 2-methyl-5-[2-(2,3-epoxypropoxy)-styryl]-1,3,4-thiadiazole and 1.5 g (0.022 mole) of 1-butynylamine-3 are reacted similarly to the Example relating to compound 3. The reaction solution is freed from an insoluble residue by filtration and is then concentrated on a rotary evaporator. This leaves 6.2 g of an oil which is purified chromatographically on Silica gel 60 (0.062–0.200 mm) from Merck, using a 4:1 mixture of chloroform and methanol as the eluant. The purified oil can be caused to crystallize by means of isopropanol-ether. 2.1 g (28% of theory). Melting point 143°–145° C.

$C_{18}H_{21}N_3O_2S$ (343)

calculated: C 62.9 H 6.2 N 12.1. found: C 61.6 H 6.2 N 12.3.

We claim:

1. 2-Methyl-5-(2-hydroxystyryl)-1,3,4-thiadiazole.

* * * * *